United States Patent
Umeda

(10) Patent No.: US 7,234,582 B2
(45) Date of Patent: Jun. 26, 2007

(54) COIN GUIDING APPARATUS

(75) Inventor: Masayoshi Umeda, Iwatsuki (JP)

(73) Assignee: Asahi Seiko Kabushiki Kaisha, Tokyo (JP)

( * ) Notice: Subject to any disclaimer, the term of this patent is extended or adjusted under 35 U.S.C. 154(b) by 520 days.

(21) Appl. No.: 10/867,329

(22) Filed: Jun. 14, 2004

(65) Prior Publication Data

US 2005/0020199 A1 Jan. 27, 2005

(30) Foreign Application Priority Data

Jun. 20, 2003 (JP) .............................. 2003-175653

(51) Int. Cl.
*G07F 1/04* (2006.01)
(52) U.S. Cl. ............................ 194/344; 453/9; 453/18; 193/2 R; 193/34; 193/DIG. 1
(58) Field of Classification Search ................ 194/344; 453/9; 221/267; 193/2 R, 34, DIG. 1; 198/841
See application file for complete search history.

(56) References Cited

U.S. PATENT DOCUMENTS 2,734,680 A * 2/1956 Jones .......................... 232/44
4,423,816 A * 1/1984 Suttles ....................... 211/183
4,478,300 A * 10/1984 Mikami ........................ 177/59
5,425,439 A * 6/1995 Tsuchida .................... 194/344
5,558,197 A  9/1996 Rothschild et al.
5,662,520 A  9/1997 Evdokimo
5,876,275 A * 3/1999 Rasmussen .................. 453/32
6,709,324 B1 * 3/2004 Beadell ....................... 453/29

FOREIGN PATENT DOCUMENTS

JP  06-51957  7/1994

* cited by examiner

*Primary Examiner*—Patrick Mackey
*Assistant Examiner*—Jeffrey A Shapiro

(57) ABSTRACT

A coin guiding channel receives coins dispensed from a coin hopper. A base plate, a first spacer, a second spacer, and a supporting plate have surfaces defining a somewhat rectangular coin guiding channel along a longitudinal axis of the base plate. The supporting plate has a first protruding section extending toward the coin guiding channel and extending along the longitudinal axis of the base plate for providing increased strength and resistance to physical distortion of the coin guiding channel. A portion of the coin guiding channel is oriented vertically and guides the received coins to a position above the coin hopper.

21 Claims, 4 Drawing Sheets

COIN GUIDING APPARATUS

CROSS-REFERENCE TO RELATED APPLICATION

This application is based on application number 2003-175653 filed in Japan, dated Jun. 20, 2003.

FIELD OF THE INVENTION

This invention is related to a coin guiding apparatus and more particularly to a coin guiding apparatus having a resistance to bending or distortion of a coin guiding channel.

DESCRIPTION OF RELATED ART

Traditional coin escalators, and coin hoppers dispensing coins into coin guiding passageways, are known. However, coin guiding passageways are prone to twisting and bending that distorts the passageway causing the jamming of coins. This is especially true when the coin guiding passageway is oriented vertically. Examples of the related art include the Japanese Laid Open Utility model No. 06-51957 (FIGS. 2-4 and pages 5-7), U.S. Pat. No. 5,662,520 to Evodokimo (FIGS. 1-2), and U.S. Pat. No. 5,558,197 to Rothschile et al. (FIGS. 2-4).

Attempted solutions to these problems have included using more rigid materials, thicker materials, and gently sloping any curving sections to prevent "shingling" where the leading edge of one coin in the coin passageway overtakes the lagging edge of a previously dispensed coin in the coin guiding passageway causing a jamming condition. Further, the coin guiding passageway width has been difficult to adjust accurately due to the elongated nature of the coin guiding passageway, and proper adjustment or alignment of the spacers was awkward.

SUMMARY OF THE INVENTION

The present invention, as defined in the claims, overcomes the deficiencies of the prior art by providing a protruding section including an observation window in a supporting plate in order to increase the strength and resistance to distortion of the coin guiding apparatus as well as other benefits and results as detailed below. A coin dispensing apparatus includes a coin hopper unit and a coin guiding unit. The coin hopper unit includes a storing bowl for storing a supply of coins and a rotating dispensing disk that receives coins from the storing bowl and dispenses coins in a one-by-one manner to a first end of the coin guiding unit. The present invention is not limited to only a coin hopper unit, and may be drawn to another embodiment utilizing the features and advantages as herein described. Similarly, the present invention is not limited to a rotating dispensing disk, but will function with an equivalent dispensing apparatus where the coins are dispensed in a one-by-one manner.

An embodiment of the present invention includes a base plate having a longitudinal axis and a surface forming a first boundary of a coin guiding channel along the longitudinal axis. The coin guiding channel receives and guides a coin with a predetermined coin thickness and a predetermined coin diameter. A first spacer has a predetermined spacer thickness and is positioned on the base plate parallel to the longitudinal axis. The spacer thickness is slightly larger than the coin thickness. A second spacer member has the corresponding spacer thickness and is positioned on the base plate parallel to the longitudinal axis at a spacing distance from the first spacer member. The spacing distance is slightly larger than the coin diameter.

The second spacer member has a surface forming a third boundary for the coin guiding channel opposite to the first spacer surface. A supporting plate is positioned adjacent to the first spacer and the second spacer and is positioned opposite the base plate. The supporting plate has a surface forming a fourth boundary for the coin guiding channel. The supporting plate has a first protruding section extending toward the coin guiding channel and extending along the longitudinal direction of the base plate for providing increased strength and resistance to physical distortion under an applied physical load or force.

Alternatively, the first protruding section can extend away from the coin guiding channel and extend along the longitudinal direction of the base plate. A portion of the coin guiding channel can be oriented vertically, directing the guided coins to a position higher than the coin hopper containing the supply of coins. In another embodiment, the coin guiding apparatus includes a curved section guiding unit and a straight section guiding unit with one or more separate supporting plates for each unit.

In another embodiment, the second spacer has an alignment tab that extends into a corresponding elongated alignment hole. The alignment hole has teeth projecting towards the center portion of the alignment hole forming alignment stops for adjusting the spacing between the first and second spacers.

In another embodiment, a holding unit is used to prevent coins from slipping backwards along the coin guiding channel. This is especially beneficial when a portion of the coin guiding channel is oriented vertically, and the gravitational force pulling against the advancing coins is maximized. Further, for each additional coin in the coin guiding channel an incremental amount of weight, corresponding to the weight of each coin, is added as a dispensing load upon the coin hopper and a rotating dispensing disk. Although the accumulated weight of the coins must be borne at some point during dispensing and advancing the column of edge-wise oriented coins, the holding unit limits the amount of weight that must be borne continuously and avoids jamming at the dispensing point of the coin hopper unit.

In another embodiment, the supporting plate may be constructed with a wave-like structure having projections alternately towards and away from the coin guiding channel. The projections away from the coin guiding channel can be rounded in shape in order to provide increased elasticity to the supporting plate. The projections toward the coin guiding channel can be flattened in shape in order to provide a piecewise planar surface facing a coin in the coin guiding channel.

In accordance with an embodiment of the present invention, the base plate can include a second protruding section extending away from the guiding channel in order to provide increased strength and resistance to physical distortion, including bending, twisting, and stretching by increasing the effective Young's modulus of the corresponding structure. The first protruding section and the second protruding section can be rectangular in shape to permit economical manufacture of the component parts through a steel stamping process, for example. The depth of protrusion of the first protruding section can be different between a portion of the coin guiding channel at the curved section guiding unit and a portion of the coin guiding channel at the straight section guiding unit.

In accordance with another embodiment, the present invention includes an interlocking unit for mating a first end of the coin guiding unit with the coin hopper unit. The interlocking unit includes interlocking tabs on the ends of the first spacer, second spacer, and the supporting plate closest to the coin hopper unit. The interlocking tabs allow the coin guiding unit to be releasably mounted on the coin hopper unit.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the intention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1:
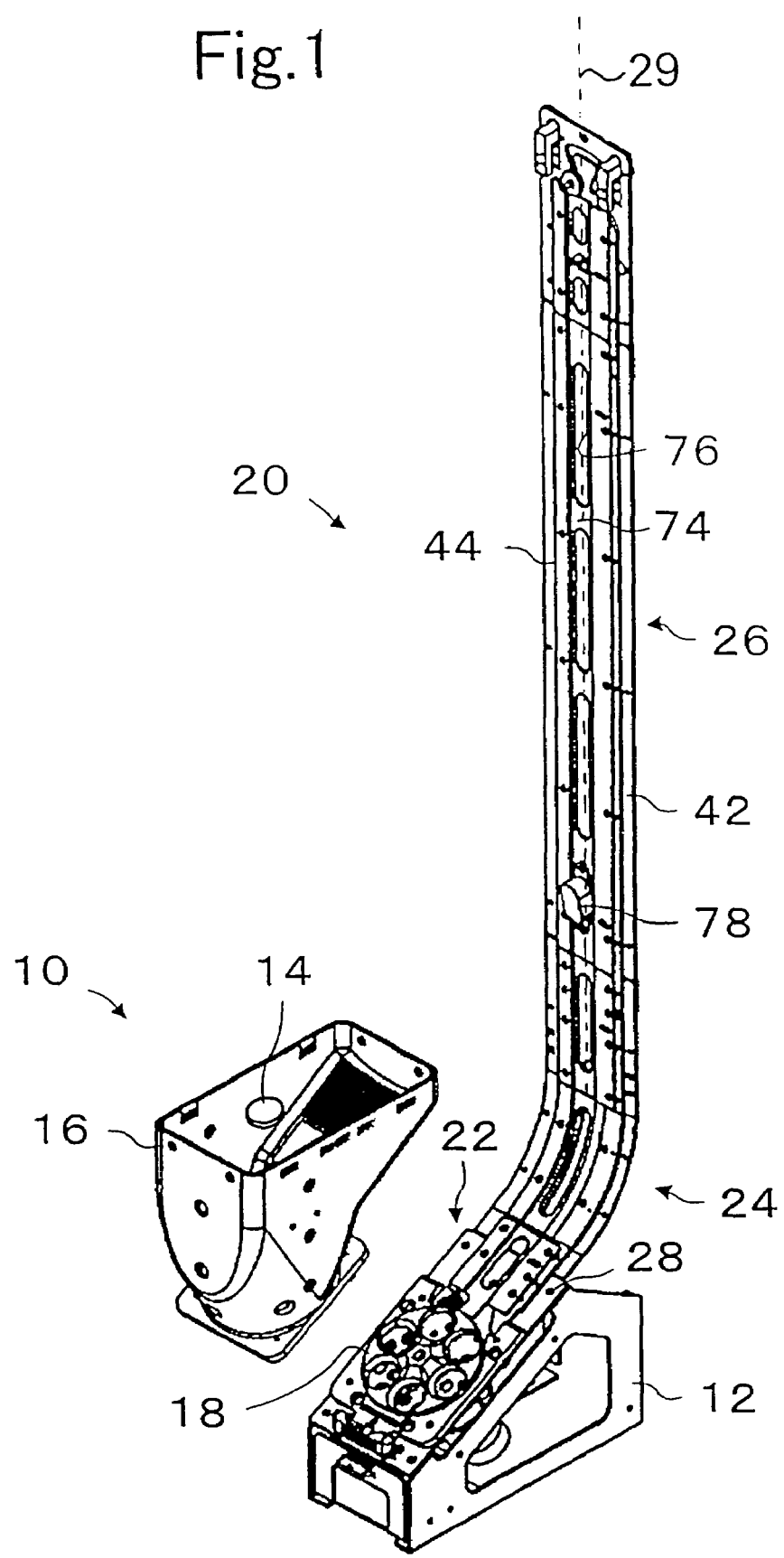
FIG. 1 is a partially exploded perspective view of coin guiding apparatus attached to a coin hopper unit showing the curved section guiding unit and the straight section guiding unit in accordance with an embodiment of the present invention.

In reference to FIG. 1, a coin hopper unit 10 and a coin guiding unit 20 are shown in accordance with an embodiment of the present invention. The coin hopper unit 10 includes a storing bowl 16 for storing a supply of coins 14 and a rotating dispensing disk 18 located in an inclined position at the bottom section of the storing bowl 16. It is understood in this description the term coin 14 includes the use of coins, tokens, medallions, chips, and any other coin-like media that may dispensed from a coin hopper unit 10 and guided as described. The storing bowl 16 stores a quantity of coins 14 in bulk and is mounted over a rotating dispensing disk 18 that is attached to a base unit 28 on a frame 12. The rotating dispensing disk 18 receives the coins 14 from the storing bowl 16 and dispenses coins 14 to the coin guiding unit in a one-by-one manner.

A slanting section guiding unit 22 is removably attached to the base 28 and forms a part of a curved section guiding unit 24. The curved section guiding unit 24 and the straight section guiding unit 26 form a part of the coin guiding unit 20 and enable coins 14 dispensed from the coin hopper 10 to be transported along a coin guiding channel 29, first at an inclined angle through the slanting section guiding unit 22, next through the curved section guiding unit 24 at a steeper angle, and finally to a vertically transported path to the straight section guiding unit 26.

Coins 14 are dispensed in a one-by-one manner into the first end of the coin guiding channel 29. Thus, the coin guiding unit 20 transports coins 14 received from the rotating dispensing disk 18 at an inclined angle to a vertical orientation along the coin guiding channel 29. The curved section guiding unit 24 and the straight section guiding unit 26 are detachable from each other for ease of manufacture and transport. The top portion of the straight section guiding unit 26 may be affixed to a portion of a gaming or entertainment machine (not shown). The length of the coin guiding unit 20, or the height of the coin dispensing point, may be changed by altering the length of the straight section guiding unit 26.

Coins 14 within the guiding channel are advanced along the coin guiding channel 29 as subsequent coins 14 are dispensed by the rotating dispensing disk 18. For example, a first coin 14 is dispensed into an empty guiding channel and rests in a position nearly adjacent to the rotating dispensing disk 18. A second coin 14 is dispensed into the coin guiding channel and pushes the first coin along the coin guiding channel 29. This process of dispensing new coins and pushing previously dispensed coins continues until the coin guiding channel 29 is full of coins. Once the coin guiding channel 29 is full of coins, dispensing a subsequent coin 14 from the rotating dispensing disk 18 will cause the first coin to be dispensed from the coin guiding channel 29 into a receptacle (not shown). This receptacle can be a bin, another coin hopper 10, or a launching point for letting the dispensed coins 14 fall under the force of gravity through an amusement device or a display, for example.

The straight section guiding unit 20 includes a straight section base plate 42 and a straight section supporting plate 44. The straight section supporting plate 44 is placed on top of the straight section base plate 42 to form the top and bottom, respectively, of the coin guiding channel 29. Spacers (30, 32) between the straight section supporting plate 44 and the straight section base plate 42, forming the left and right side of the coin guiding channel 29, will be discussed below. The spacers (30, 32) can be formed as a continuous piece within each of the curved section guiding unit and the straight section guiding unit. Alternatively, the spacers (30, 32) can be formed of two or more segments within each unit. The straight section supporting plate 44 has a protruding section 74 which extends both into the coin guiding channel 29 and longitudinally along the coin guiding channel 29 with the straight section base plate 42. The descriptions of top, bottom, right, and left are for reference only and are not considered limiting.

The protruding section 74 in the straight section supporting plate 44 provides an increased resistance to deformation of the straight section supporting plate 44, and provides a more rigid structure to the guiding unit 20 so that when an external force is applied to the guiding unit 20, the coin guiding channel 29 is not significantly distorted. Essentially, the cross-section of the coin guiding channel 29 is not substantially changed, and the coins 14 can advance smoothly through the coin guiding channel 29. Similarly, the rest of the guiding unit 20 consists of a series of plates covered by plates with similar protruding sections as will be described in greater detail below.

Within the straight section supporting plate 44 is an observation window 76 that allows coins 14 within the coin guiding channel 29 to be visible from the front of the apparatus as the coins 14 are pushed along the coin guiding channel 29. Near a lower portion of the straight section guiding unit 26 is a holding unit 78 for preventing coins 14 from regressing along the coin guiding channel 29. The holding unit permits coins to pass along the coin guiding channel 29 in a first direction away from the coin hopper 10 while inhibiting coins from passing along the coin guiding channel 29 in a second direction opposite to the first direction. Since a portion of the coin guiding unit can be extended vertically, the holding unit prevents advancing coins from regressing back towards the coin hopper unit 10.

Figure 2:
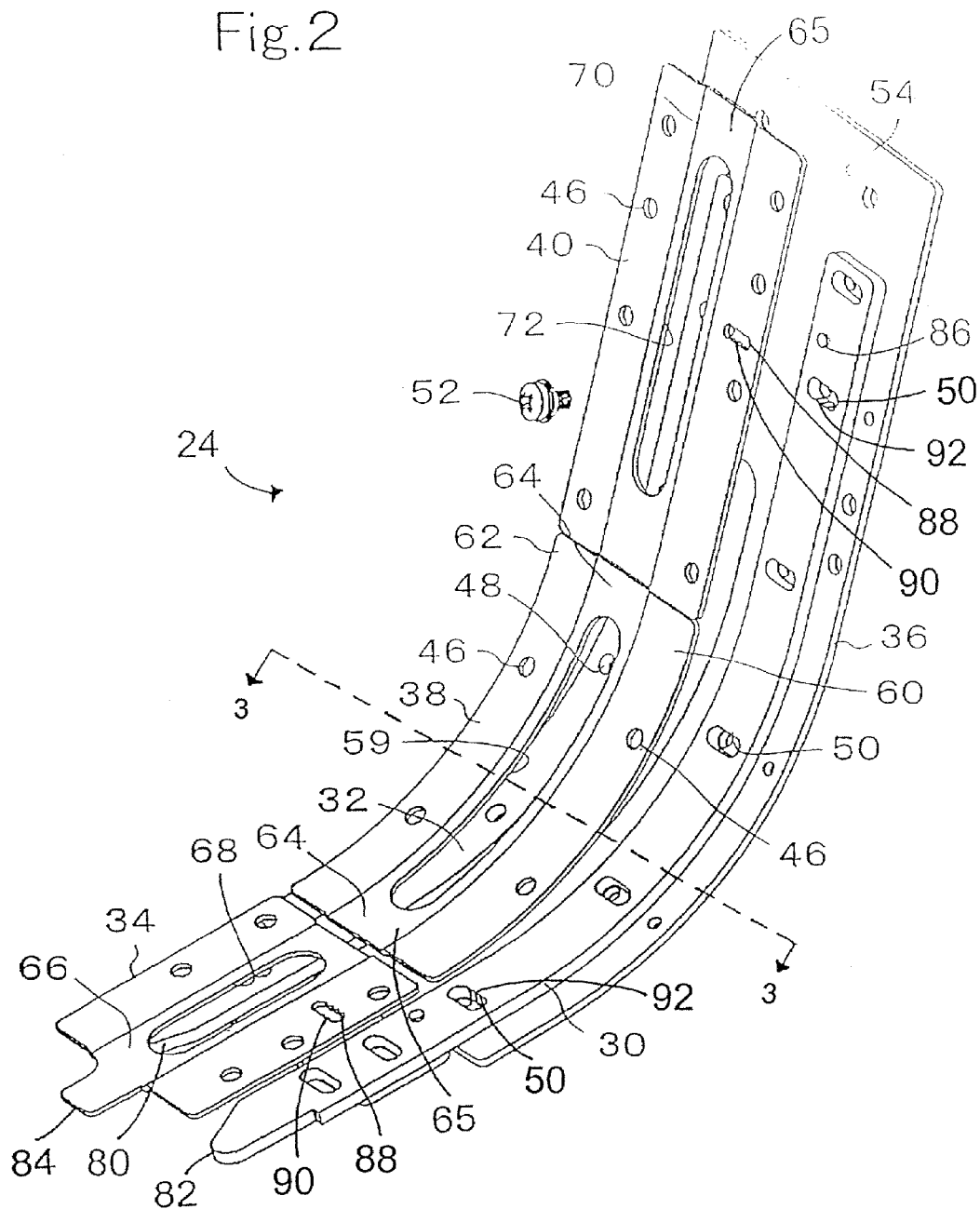
FIG. 2 is an exploded perspective view of the curved section guiding unit in accordance with an embodiment of the present invention.

In reference to FIG. 2, the curved section guiding unit 24 is explained. The curved section guiding unit 24 includes a curved section base plate 36 having a surface with a curved shape that forms the bottom of the coin guiding channel 29 through the curved section guiding unit 24. The top surface of the base plate 36 is a first surface forming a boundary for the coin guiding channel 29. Mounted upon the curved section base plate 36 are a right spacer member 30 and a left spacer member 32 forming the right side and left side, respectively, of the coin guiding channel 29. The right surface of the left spacer 32 forms a second surface forming a boundary for the coin guiding channel 29 while the left surface of the right spacer 30 forms a third surface forming a boundary for the coin guiding channel 29.

Similar to the straight section guiding unit 26 above, the curved section guiding unit 24 has a number of covering plates forming the top side of the coin guiding channel 29. The bottom surface of the supporting plates form a fourth surface forming a boundary for the coin guiding channel 29. The first surface, second surface, third surface, and fourth surface together define the substantially rectangular coin guiding channel 29. Specifically, the top plates include a slanting section support plate 34, a curved section supporting plate 38, and a curved section straight supporting plate 40. Each of the plates has holes 46 for mounting the plates on top of the spacers (30, 32) and onto the curved section base plate 36.

Screws 52 are pushed through each hole 46 in the supporting plates (24, 28, 46) and through either a corresponding hole 48 in the left spacer member 32 or a through an elongated hole 50 in the right spacer 30 to be threaded into their corresponding threaded hole 54 in the curved section base plate 36. The elongated hole extends at a right angle to the longitudinal axis of the coin guiding channel 29 to permit adjustment of the right spacer 30. When tightened, the screws 52 hold the supporting plates (24, 28, 46), the spacers (30, 32), and the base plates (36, 42) together. The spacers (30, 32) have a predetermined thickness to accommodate the expected thickness of a valid coin 14. Similarly, the spacers (30, 32) are spaced a predetermined distance apart on the curved section base plate 36 to accommodate the expected diameter of a valid coin 14.

Each of the coverplates (34, 38, 46) has a right side 60 and a left side 62 that mount over their corresponding section of each spacer (30, 32). Protruding sections (64, 66, 70) are formed between the corresponding right side 60 and the left side 62 of each coverplate. As discussed above, the protruding sections can extend both toward and longitudinally along the coin guiding channel 29. The protruding sections (64, 66, 70) provide increased structural strength and resistance to deformation. Each coverplate also has an observation window (59, 68, 72) for viewing the coins 14 along the coin guiding channel 29. The structure of the observation window 59 within the protruding section 64 of the curved section supporting plate 38 defines a stay section 65 at both ends. The stay sections 65 provide strength between the right side section 60 and left side section 62 while reducing the weight and cost of the curved section supporting plate 38.

The observation window 59 is located near the middle in the longitudinal axis of curved section supporting plate 38. The descriptions herein of the components of the curved section guiding unit 24 also apply by analogy to the structure of similar components within the structure such as the straight section guiding unit 26. However, the depth of protrusion of the protruding section 64 of the curved section supporting plate 38 is different from the depth of protrusion in the straight section supporting plate 44, as will be described in more detail below.

The slanting section guiding unit 22 has a set of interlocking tabs (80, 82, 84) for releasably mating with the coin hopper unit 10. A first interlocking tab 80 is formed on the end of the left spacer 32 adjacent to the rotating dispensing disk 18. A second interlocking tab 82 is formed on the end of the right spacer 30 adjacent to the dispensing area of the rotating dispensing disk 18. Finally, a third interlocking tab 84 is formed on the end of the slanting section support plate 34. These interlocking tabs (80, 82, 84) provide for proper alignment with the rotating dispensing disk 18 so that a dispensed coin 14 is received into the coin guiding channel 29.

Figure 3:
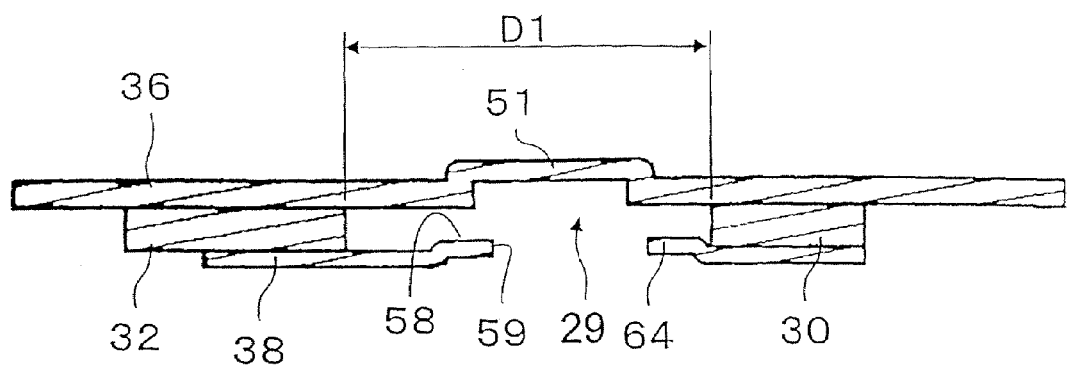
FIG. 3 is a lateral cross sectional view along the line 3-3 shown in FIG. 2 in accordance with an embodiment of the present invention.

In reference to FIG. 3, a lateral cross sectional view shows a portion of the coin guiding channel 29 is enclosed by surfaces of the curved section base plate 36, the right spacer 30, the left spacer 32, and the curved section supporting plate 38 to provide a somewhat rectangular passageway crossing the coin guiding channel 29 at a right angle. In this case, the right spacer 30 is moved to its closest point to the left spacer 32. A concave groove 51 is located near the middle point of and extends longitudinally along the curved section base plate 36 to provide support for and resistance to distortion of the coin guiding channel 29 caused by a force. The concave groove 51 can be considered a second protruding section 51 that extends away from the coin guiding channel 29. Both the first protruding section 64 and the second protruding section 51 are somewhat rectangular in shape with a flattened center portion of the protruding sections and squared sides. This construction may be accomplished economically by stamping steel blanks into the proper shape, for example.

A guiding section 58 is on a surface of the curved section supporting plate 38 and faces to the coin guiding channel 29. The guiding section 58 is formed adjacent to the observation window 59 and both protrudes towards the curved section base plate 36 and extends longitudinally along the longitudinal axis of the curved section base plate 36. A coin 14 is guided along the coin guiding channel 29 when a surface of the coin 14 contacts a surface of the coin guiding channel 29. If the coin 14 is thick, the protruding section 64 may extend in a direction opposite the curved section base plate 36 and away from the coin guiding channel 29. In this case, the structural improvement, providing added strength and resistance to distortion, of the coin guiding unit 20 is maintained while accommodating a larger coin 14.

Further, to accommodate a coin 14 having a different thickness, the spacers (30, 32) may be changed to a different thickness, and/or the depth of protrusion of the protruding section 64 may be changed based on the movement of the coin 14. The distance D1 between the surfaces of the spacers (30, 32) is slightly larger than the diameter of a valid coin 14. A valid coin is one that is expected, while an invalid coin would be a fraudulently used token or simply a coin of a different denomination than the expect coin. When a new coin 14 is used having a different diameter, the distance D1 can be changed by loosening the screws 52 for the right spacer member 30 and moving the right spacer 30 toward or away from the coin guiding channel 29 and retightening the screws 52.

The surface of the right spacer 30 includes an alignment tab 86 that extends from the right spacer 30 through an elongated alignment hole 88 in the mating curved section straight supporting plate 40 to provide an indication of the distance between the right spacer 30 and the left spacer 32. This indication can be a series of hash marks outside the elongated hole 88, for example, to indicate a measurement value. The elongated alignment hole 88 includes a number of teeth 90 for providing alignment stops to facilitate proper alignment of the right spacer 30 to the desired distance D1. Similarly, the elongated hole 50 corresponding to the alignment tab 86 and elongated alignment hole 90 has teeth 92 projecting towards the center portion of the elongated alignment hole 88. In this manner, the left spacer 32 is fixed, while the right spacer 30 is adjustable within the length of the elongated holes 50.

Figure 5:
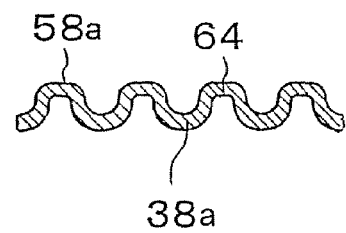
FIG. 5 is a lateral cross section view of the curved section supporting plate in accordance with an embodiment of the present invention.

In an alternative embodiment, the surface of the curved section supporting plate 38 can be made into a wave-like pattern as shown in FIG. 5. This has the benefit of reducing the contact surface of the guiding section 58*a* with a passing coin 14 in the coin guiding channel 29, thereby reducing the friction with the coin 14 and the amount of debris deposits that may be collected from the passing coins 14. The projections 38*a* away from the coin guiding channel 29 can be rounded in shape in order to provide increased elasticity to the supporting plate. The projections 58*a* toward the coin guiding channel 29 can be flattened in shape in order to provide a piecewise planar surface facing a coin in the coin guiding channel.

Figure 4:
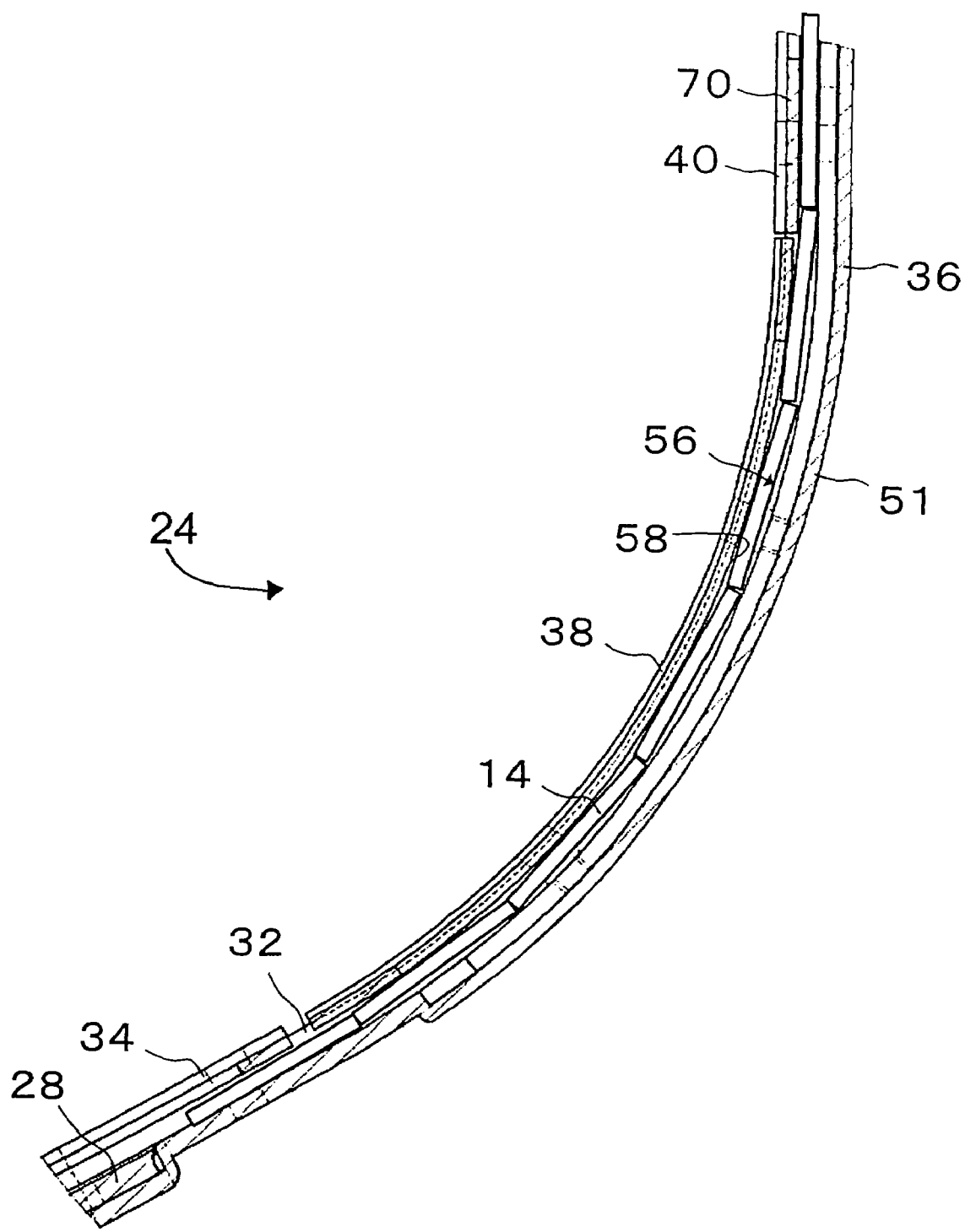
FIG. 4 is a longitudinal cross section view of the curved section guiding unit containing coins that are advanced through the coin guiding channel in accordance with an embodiment of the present invention.

In reference to FIG. 4, a longitudinal cross sectional view of the coin guiding channel 29 within the curved section guiding unit 24 is shown full of coins 14. When a coin 14 is guided by the curved section guiding unit 24, the leading and the lagging ends of the coin 14 are guided by the base plate 36 while the middle section of the coin 14 is guided by the curved section supporting plate 38. The diameter of the valid coin determines the curving ratio since the valid coin cannot traverse the coin guiding channel through a curved section if excessive friction occurs due to jamming of the coin into the coin guiding channel 29. Therefore, the depth of protrusion of the protruding section 64 is less for the curved section supporting plate 38 than the depth of protrusion of the protruding section 70 within the curved section straight supporting plate 40.

Effectively, the thickness of the coin 14, is defined as the closest, minimum distance between the curved section base plate 36 and the curved section supporting plate 38, is increased by traveling adjacent to the surface of the curved portion of the curved section base plate 36. In this way, only the straight section supporting plate 44 can be changed because curved section supporting plate 38 is separated from straight section supporting plate 44 of straight section guiding unit 26 and the thickness of the coin guiding channel 29 can be easily changed by changing the protruding amount of supporting plates (38, 40, 44). Alternatively, a supply of supporting plates may be provided given the expected use with a known coin currency scheme.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A coin guiding apparatus for guiding a plurality of coins along a coin guiding channel, the plurality of coins being dispensed from a coin hopper in a one-by-one manner and guided to a position above the coin hopper, the coin guiding apparatus comprising:
   a base plate having a longitudinal axis, the base plate having a surface forming a first boundary of a coin guiding channel along the longitudinal axis, the coin guiding channel being capable of receiving and guiding a coin with a predetermined coin thickness and a predetermined coin diameter;
   a first spacer member having a predetermined spacer thickness and operatively positioned on the base plate parallel to the longitudinal axis, the spacer thickness being slightly larger than the coin thickness, the first spacer member having a surface forming a second boundary for the coin guiding channel;
   a second spacer member having the same spacer thickness and operatively positioned on the base plate parallel to the longitudinal axis at a predetermined spacing distance from the first spacer member, the spacing distance being slightly larger than the coin diameter, the second spacer member having a surface forming a third boundary for the coin guiding channel opposite to the first spacer member surface; and
   a supporting plate operatively positioned adjacent to the first spacer member and the second spacer member and positioned opposite the base plate, the supporting plate having a surface forming a fourth boundary for the coin guiding channel, the supporting plate having a first protruding section extending toward the coin guiding channel and extending along the longitudinal axis of the base plate for providing increased strength and resistance to physical distortion of the coin guiding channel, wherein the base plate includes a second protruding section extending along the coin guiding channel to further provide increased strength and resistance to physical distortion of the coin guiding channel.

2. The apparatus of claim 1, further comprising:
   a plurality of supporting plates operatively mounted on the base plate.

3. The apparatus of claim 2, further comprising:
   a curved section supporting plate; and
   a straight section supporting plate,
   wherein a predetermined portion of the base plate is curved and defines a curved section guiding unit for guiding the plurality of coins along a curved path along the longitudinal axis; and
   wherein a predetermined portion of the base plate is straight and defines a straight section guiding unit for guiding the plurality of coins along a straight path along the longitudinal axis,
   wherein the curved section supporting plate is adjacent to the portion of the curved section guiding unit and the straight section supporting plate is adjacent to the portion of the straight section guiding unit.

4. The apparatus of claim 2, wherein each of the plurality of supporting plates includes a first side section for mounting adjacent to the first spacer member and a second side section for mounting adjacent to the second spacer member.

5. The apparatus of claim 4, each of the plurality of supporting plates further comprising:
an observation window within the first protruding section and extending along the coin guiding channel for viewing coins disposed within the coin guiding channel.

6. A coin guiding apparatus for guiding a plurality of coins along a coin guiding channel, the plurality of coins being dispensed from a coin hopper unit in a one-by-one manner and guided to a position above the coin hopper unit, the coin guiding apparatus comprising:
a base plate having a longitudinal axis, the base plate having a surface forming a first boundary of a coin guiding channel along the longitudinal axis, the coin guiding channel being capable of receiving and guiding a coin with a predetermined coin thickness and a predetermined coin diameter;
a first spacer member having a predetermined spacer thickness and operatively positioned on the base plate parallel to the longitudinal axis, the spacer thickness being slightly larger than the coin thickness, the first spacer member having a surface forming a second boundary for the coin guiding channel, the first spacer member being fixed on the base plate;
a second spacer member having the same spacer thickness and operatively positioned on the base plate parallel to the longitudinal axis at a predetermined spacing distance from the first spacer member, the spacing distance being slightly larger than the coin diameter, the second spacer member having a surface forming a third boundary for the coin guiding channel opposite to the first spacer member surface, the second spacer member being adjustable on the base plate, the spacing distance being adjustable to accommodate coins of varying diameter; and
a plurality of sequentially aligned supporting plates operatively positioned adjacent to the first spacer member and the second spacer member and positioned opposite the base plate, each of the supporting plates having a surface forming a fourth boundary for the coin guiding channel, each of the supporting plates have a first protruding section extending toward the coin guiding channel and extending along the longitudinal axis of the base plate for providing increased strength and resistance to physical distortion of the coin guiding channel, wherein the base plate includes a continuous second protruding section extending along the coin guiding channel, the first and second protruding sections define a cross sectional area of the coin guiding channel traverse to the longitudinal axis of the coin guiding channel.

7. The apparatus of claim 6, further comprising:
a curved section guiding unit for guiding the plurality of coins along a curved path on the longitudinal axis of the base plate, the curved section guiding unit having a curved section supporting plate; and
a straight section guiding unit for guiding the plurality of coins along a straight path on the longitudinal axis of the base plate, the straight section guiding unit having a straight section supporting plate that is separated from the curved section supporting plate.

8. The apparatus of claim 6, further comprising:
an alignment tab mounted on the second spacer member; and
an elongated alignment hole in a mating supporting plate for receiving the alignment tab, the elongated alignment hole having a plurality of teeth projecting towards the center portion of the elongated alignment hole at a predetermined spacing, the plurality of teeth providing a plurality of alignment stops for adjusting the predetermined spacing distance between the fixed first spacer member and the adjustable second spacer member.

9. The apparatus of claim 6, further comprising:
a holding unit disposed along the coin guiding channel for preventing coins from regressing along the coin guiding channel, the holding unit permitting coins to pass along the coin guiding channel in a first direction while inhibiting coins from passing along the coin guiding channel in a second direction opposite to the first direction.

10. The apparatus of claim 6, wherein the supporting plate further comprises:
a wave-like structure with projections alternately towards the coin guiding channel and away from the coin guiding channel for providing structural strength and resistance to physical distortion.

11. The apparatus of claim 10, wherein the projections extend alternately towards the coin guiding channel and away from the coin guiding channel, further comprising:
the projections away from the coin guiding channel being rounded in shape for providing an increased elasticity to the supporting plate; and
the projections toward the coin guiding channel being flattened in shape for providing a piecewise planar surface facing the coin guiding channel.

12. The apparatus of claim 6, wherein the first protruding section extends away from the guiding channel for providing increased strength and resistance to physical distortion.

13. The apparatus of claim 7, wherein the depth of protrusion toward the coin guiding channel for the first protruding section is different between a portion of the coin guiding channel at the curved section guiding unit and the straight section guiding unit.

14. The apparatus of claim 6, wherein a predetermined portion of the coin guiding channel is oriented vertically.

15. The apparatus of claim 6, further comprising:
a first interlocking tab on a first end of the first spacer member;
a second interlocking tab on a first end of the second spacer member;
a third interlocking tab on a first end of the supporting plate,
wherein the first interlocking tab, the second interlocking tab, and the third interlocking tab form an interlocking tab unit for releasably mating with the coin hopper unit.

16. The apparatus of claim 7, wherein the depth of protrusion toward the coin guiding channel for the first protruding section is different between a portion of the coin guiding channel at the curved section guiding unit and the straight section guiding unit.

17. The apparatus of claim 7, wherein the base plate further comprising:

the second protruding section extends away from the coin guiding channel for providing increased strength and resistance to physical distortion.

18. The apparatus of claim 17,
wherein first protruding section and the second protruding section have a substantially rectangular shape.

19. The apparatus of claim 6 further including a holding unit disposed along the coin guiding channel for preventing coins from regressing along the coin guiding channel, the holding unit permitting coins to pass along the coin guiding channel in a first direction while inhibiting coins from passing along the coin guiding channel in a second direction opposite to the first direction.

20. The apparatus of claim 1 wherein the first protruding section and the second protruding section are aligned over the coin guiding channel and extend in the same direction traverse to the longitudinal axis of the coin guiding channel.

21. A coin dispensing apparatus, comprising:
a coin hopper unit including a storing bowl for storing a supply of coins, the coin hopper unit including a rotating dispensing disk for receiving coins from the storing bowl and dispensing coins from the coin hopper unit in a one-by-one manner; and
a coin guiding unit for receiving coins dispensed by the coin hopper unit and guiding the dispensed coins to a position above the coin hopper, comprising:
a curved base plate having a longitudinal axis, the curved base plate having a surface forming a first boundary of a coin guiding channel along the longitudinal axis, the coin guiding channel being capable of receiving and guiding a coin with a predetermined coin thickness and a predetermined coin diameter;
a curved first spacer member having a predetermined spacer thickness and operatively positioned on the curved base plate parallel to the longitudinal axis, the spacer thickness being slightly larger than the coin thickness, the curved first spacer member having a surface forming a second boundary for the coin guiding channel, the curved first spacer member being fixed on the curved base plate, and the curved first spacer member extends to the hopper unit further than the curved base plate;
a curved second spacer member having the same spacer thickness and operatively positioned on the curved base plate parallel to the longitudinal axis at a predetermined distance from the curved first spacer member, the spacing distance being slightly larger than the coin diameter, the curved second spacer member includes elongate holes extend to the curved first spacer member, the curved second spacer member having a surface forming a third boundary for the coin guiding channel opposite to the curved first spacer member surface, the curved second spacer member can be adjust on the curved base plate, the spacing distance being adjustable to accommodate coins of varying diameter, and the curved second spacer member extends to the hopper unit further than the curved base plate;
a curved section supporting plate operatively positioned adjacent to the curved first spacer member and the curved second spacer member and positioned opposite the curved base plate, the curved section supporting plate having a surface forming a fourth boundary for the coin guiding channel, the curved section supporting plate having a first protruding section extending toward the coin guiding channel and extending along the longitudinal axis of the curved base plate for providing increased strength and resistance to physical distortion of the coin guiding channel, an observation window within the first protruding section and extending along the coin guiding channel for viewing coins disposed within the first protruding section and extending along the coin guiding channel for viewing coins disposed within the coin guiding channel, the depth of protrusion toward the coin guiding channel for the first protruding section is different between a portion of the coin guiding channel at a curved section guiding unit and a straight section guiding unit;
a curved section straight supporting plate operatively positioned adjacent to the curved first spacer member and the curved second spacer member and positioned opposite the curved base plate; and
a slanting section supporting plate operatively positioned adjacent to the curved first spacer member and the curved second spacer member and positioned at the extending sections of the curved first spacer member and the curved second spacer member.

* * * * *